(12) United States Patent
Canovas Vidal et al.

(10) Patent No.: US 10,653,556 B2
(45) Date of Patent: May 19, 2020

(54) LENSES, SYSTEMS AND METHODS FOR PROVIDING BINOCULAR CUSTOMIZED TREATMENTS TO CORRECT PRESBYOPIA

(71) Applicant: AMO GRONINGEN B.V., Groningen (NL)

(72) Inventors: Carmen Canovas Vidal, Groningen (NL); Marrie H. Van Der Mooren, Englebert (NL); Luuk Franssen, Groningen (NL); Hendrik A. Weeber, Groningen (NL)

(73) Assignee: AMO Groningen B.V., Groningen (NL)

( * ) Notice: Subject to any disclaimer, the term of this patent is extended or adjusted under 35 U.S.C. 154(b) by 186 days.

(21) Appl. No.: 15/665,109

(22) Filed: Jul. 31, 2017

(65) Prior Publication Data

US 2017/0326002 A1 Nov. 16, 2017

Related U.S. Application Data

(62) Division of application No. 14/096,544, filed on Dec. 4, 2013, now Pat. No. 9,717,628.

(60) Provisional application No. 61/733,292, filed on Dec. 4, 2012.

(51) Int. Cl.
*A61F 9/008* (2006.01)
*A61F 2/16* (2006.01)

(52) U.S. Cl.
CPC ........ *A61F 9/00804* (2013.01); *A61F 2/1621* (2013.01); *A61F 2/1637* (2013.01); *A61F 9/00802* (2013.01); *A61F 9/00825* (2013.01); *A61F 9/00829* (2013.01); *A61F 9/00834* (2013.01); *A61F 9/00838* (2013.01); *A61F 2009/0087* (2013.01);

(Continued)

(58) Field of Classification Search
None
See application file for complete search history.

(56) References Cited

U.S. PATENT DOCUMENTS

| 2,077,092 A | 4/1937 | Broder |
| 3,305,294 A | 2/1967 | Alvarez |
| 3,367,734 A | 2/1968 | Karl et al. |

(Continued)

FOREIGN PATENT DOCUMENTS

| CA | 2722274 A1 | 10/2009 |
| CN | 1035363 A | 9/1989 |

(Continued)

OTHER PUBLICATIONS

International Search Report and Written Opinion for Application No. PCT/IB2013/003173, dated Sep. 2, 2014, 15 pages.

(Continued)

*Primary Examiner* — David H Willse
*Assistant Examiner* — Javier G Blanco
(74) *Attorney, Agent, or Firm* — Johnson & Johnson Surgical Vision, Inc.

(57) ABSTRACT

An apparatus, such as lenses, a system and a method for providing custom ocular aberrations that provide higher visual acuity. The apparatus, system and method include inducing rotationally symmetric aberrations along with an add power in one eye and inducing non-rotationally symmetric aberrations along with an add power in the other eye to provide improved visual acuity at an intermediate distance.

6 Claims, 5 Drawing Sheets

(52) U.S. Cl.
CPC .............. *A61F 2009/00872* (2013.01); *A61F 2009/00887* (2013.01); *A61F 2009/00895* (2013.01)

(56) References Cited

U.S. PATENT DOCUMENTS

| | | |
|---|---|---|
| 3,735,685 A | 5/1973 | Plummer |
| 4,010,496 A | 3/1977 | Neefe |
| 4,077,071 A | 3/1978 | Freeman |
| 4,093,361 A | 6/1978 | Erickson et al. |
| 4,134,160 A | 1/1979 | Bayers |
| 4,162,122 A | 7/1979 | Cohen |
| 4,174,543 A | 11/1979 | Kelman |
| 4,210,391 A | 7/1980 | Cohen et al. |
| 4,249,272 A | 2/1981 | Poler |
| 4,254,509 A | 3/1981 | Tennant |
| 4,254,510 A | 3/1981 | Tennant |
| 4,316,293 A | 2/1982 | Bayers |
| 4,319,564 A | 3/1982 | Karickhoff |
| 4,338,005 A | 7/1982 | Cohen |
| 4,340,283 A | 7/1982 | Cohen et al. |
| 4,370,760 A | 2/1983 | Kelman |
| 4,377,873 A | 3/1983 | Reichert |
| 4,402,579 A | 9/1983 | Poler |
| 4,403,353 A | 9/1983 | Tennant |
| 4,404,694 A | 9/1983 | Kelman |
| 4,409,691 A | 10/1983 | Levy |
| 4,424,597 A | 1/1984 | Schlegel |
| 4,446,581 A | 5/1984 | Blake |
| 4,480,340 A | 11/1984 | Shepard |
| 4,500,382 A | 2/1985 | Foster |
| 4,504,982 A | 3/1985 | Burk |
| 4,551,864 A | 11/1985 | Akhavi |
| 4,556,998 A | 12/1985 | Siepser |
| 4,560,383 A | 12/1985 | Leiske |
| 4,593,981 A | 6/1986 | Scilipoti |
| 4,605,409 A | 8/1986 | Kelman |
| 4,605,411 A | 8/1986 | Fedorov et al. |
| 4,629,460 A | 12/1986 | Dyer |
| 4,629,462 A | 12/1986 | Feaster |
| 4,636,049 A | 1/1987 | Blaker |
| 4,637,697 A | 1/1987 | Freeman |
| 4,642,112 A | 2/1987 | Freeman |
| 4,655,565 A | 4/1987 | Freeman |
| 4,673,406 A | 6/1987 | Schlegel |
| 4,676,791 A | 6/1987 | LeMaster et al. |
| 4,676,792 A | 6/1987 | Praeger |
| 4,681,102 A | 7/1987 | Bartell |
| 4,687,484 A | 8/1987 | Kaplan |
| 4,687,485 A | 8/1987 | Lim et al. |
| RE32,525 E | 10/1987 | Pannu |
| 4,725,277 A | 2/1988 | Bissonette |
| 4,734,095 A | 3/1988 | Siepser |
| 4,778,462 A | 10/1988 | Grendahl |
| 4,781,717 A | 11/1988 | Grendahl |
| 4,787,903 A | 11/1988 | Grendahl |
| 4,787,904 A | 11/1988 | Severin et al. |
| 4,795,462 A | 1/1989 | Grendahl |
| 4,798,608 A | 1/1989 | Grendahl |
| 4,798,609 A | 1/1989 | Grendahl |
| 4,828,558 A | 5/1989 | Kelman |
| 4,834,748 A | 5/1989 | McDonald |
| 4,863,539 A | 9/1989 | Lee et al. |
| 4,898,461 A | 2/1990 | Portney |
| 4,932,970 A | 6/1990 | Portney |
| 4,995,714 A | 2/1991 | Cohen |
| 4,995,715 A | 2/1991 | Cohen |
| 4,997,442 A | 3/1991 | Barrett |
| 5,016,977 A | 5/1991 | Baude et al. |
| 5,019,097 A | 5/1991 | Knight et al. |
| 5,047,052 A | 9/1991 | Dubroff |
| 5,054,905 A | 10/1991 | Cohen |
| 5,056,908 A | 10/1991 | Cohen |
| 5,066,301 A | 11/1991 | Wiley |
| 5,071,432 A | 12/1991 | Baikoff |
| 5,078,742 A | 1/1992 | Dahan |
| 5,089,023 A | 2/1992 | Swanson |
| 5,096,285 A | 3/1992 | Silberman |
| 5,114,220 A | 5/1992 | Baude et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,133,749 A | 7/1992 | Nordan |
| 5,144,483 A | 9/1992 | Cohen |
| 5,147,395 A | 9/1992 | Willis |
| 5,147,397 A | 9/1992 | Christ et al. |
| 5,184,405 A | 2/1993 | Cress |
| 5,197,981 A | 3/1993 | Southard |
| 5,201,763 A | 4/1993 | Brady et al. |
| 5,203,790 A | 4/1993 | McDonald |
| 5,217,491 A | 6/1993 | Vanderbilt |
| 5,225,858 A | 7/1993 | Portney |
| 5,225,997 A | 7/1993 | Lederer et al. |
| 5,229,797 A | 7/1993 | Futhey et al. |
| 5,258,025 A | 11/1993 | Fedorov et al. |
| 5,278,592 A | 1/1994 | Marie et al. |
| 5,408,281 A | 4/1995 | Zhang |
| 5,433,745 A | 7/1995 | Graham et al. |
| 5,476,513 A | 12/1995 | Brady et al. |
| 5,479,220 A | 12/1995 | Komatsu et al. |
| 5,567,365 A | 10/1996 | Weinschenk, III et al. |
| 5,571,177 A | 11/1996 | Deacon et al. |
| 5,620,720 A | 4/1997 | Glick et al. |
| 5,628,796 A | 5/1997 | Suzuki |
| 5,652,638 A | 7/1997 | Roffman et al. |
| 5,691,800 A | 11/1997 | Iki et al. |
| 5,699,142 A | 12/1997 | Lee et al. |
| 5,715,031 A | 2/1998 | Roffman et al. |
| 5,716,403 A | 2/1998 | Tran et al. |
| 5,748,282 A | 5/1998 | Freeman |
| 5,760,871 A | 6/1998 | Kosoburd et al. |
| 5,796,462 A | 8/1998 | Roffman et al. |
| 5,801,807 A | 9/1998 | Satake et al. |
| 5,928,282 A | 7/1999 | Nigam |
| 5,968,094 A | 10/1999 | Werblin et al. |
| 6,015,435 A | 1/2000 | Valunin et al. |
| 6,051,024 A | 4/2000 | Cumming |
| 6,055,111 A | 4/2000 | Nomura et al. |
| 6,126,283 A | 10/2000 | Wen et al. |
| 6,126,286 A | 10/2000 | Portney |
| 6,129,759 A | 10/2000 | Chambers |
| 6,142,625 A | 11/2000 | Sawano et al. |
| 6,179,870 B1 | 1/2001 | Sourdille et al. |
| 6,210,005 B1 | 4/2001 | Portney |
| 6,235,055 B1 | 5/2001 | Chu |
| 6,261,321 B1 | 7/2001 | Kellan |
| 6,319,282 B1 | 11/2001 | Nishi |
| 6,338,559 B1 | 1/2002 | Williams et al. |
| 6,419,697 B1 | 7/2002 | Kelman |
| 6,457,826 B1 | 10/2002 | Lett |
| 6,464,355 B1 | 10/2002 | Gil |
| 6,474,814 B1 | 11/2002 | Griffin |
| 6,488,708 B2 | 12/2002 | Sarfarazi |
| 6,491,721 B2 | 12/2002 | Freeman et al. |
| 6,527,389 B2 | 3/2003 | Portney |
| 6,533,416 B1 | 3/2003 | Fermigier et al. |
| 6,536,899 B1 | 3/2003 | Fiala |
| 6,537,317 B1 * | 3/2003 | Steinert .................. A61F 2/145 623/6.24 |
| 6,547,822 B1 | 4/2003 | Lang |
| 6,554,859 B1 | 4/2003 | Lang et al. |
| 6,557,992 B1 | 5/2003 | Dwyer et al. |
| 6,598,606 B2 | 7/2003 | Terwee et al. |
| 6,609,793 B2 | 8/2003 | Norrby et al. |
| 6,705,729 B2 | 3/2004 | Piers et al. |
| 6,709,102 B2 | 3/2004 | Duppstadt |
| 6,802,605 B2 | 10/2004 | Cox et al. |
| 6,808,262 B2 | 10/2004 | Chapoy et al. |
| 6,830,332 B2 | 12/2004 | Piers et al. |
| 6,846,326 B2 | 1/2005 | Zadno-Azizi et al. |
| 6,851,803 B2 | 2/2005 | Wooley et al. |
| 6,899,425 B2 | 5/2005 | Roffman et al. |
| 6,923,539 B2 | 8/2005 | Simpson et al. |

(56) References Cited

U.S. PATENT DOCUMENTS

| | | |
|---|---|---|
| 6,923,540 B2 | 8/2005 | Ye et al. |
| 6,986,578 B2 | 1/2006 | Jones |
| 7,036,931 B2 | 5/2006 | Lindacher et al. |
| 7,048,760 B2 | 5/2006 | Cumming |
| 7,061,693 B2 | 6/2006 | Zalevsky |
| 7,073,906 B1 | 7/2006 | Portney |
| 7,137,702 B2 | 11/2006 | Piers et al. |
| 7,156,516 B2 | 1/2007 | Morris et al. |
| 7,188,949 B2 | 3/2007 | Bandhauer et al. |
| 7,287,852 B2 | 10/2007 | Fiala |
| 7,293,873 B2 | 11/2007 | Dai et al. |
| 7,365,917 B2 | 4/2008 | Zalevsky |
| 7,377,640 B2 | 5/2008 | Piers et al. |
| 7,441,894 B2 | 10/2008 | Zhang et al. |
| 7,455,404 B2 | 11/2008 | Bandhauer et al. |
| 7,455,407 B2 | 11/2008 | Neal et al. |
| 7,475,986 B2 | 1/2009 | Dai et al. |
| 7,615,073 B2 | 11/2009 | Deacon et al. |
| 7,616,330 B2 | 11/2009 | Neal et al. |
| 7,713,299 B2 | 5/2010 | Brady et al. |
| 7,794,497 B2 | 9/2010 | Brady et al. |
| 7,857,451 B2 | 12/2010 | Thibos et al. |
| 7,871,162 B2 | 1/2011 | Weeber |
| 7,993,398 B2 | 8/2011 | Deacon et al. |
| 8,002,827 B2 | 8/2011 | Deacon et al. |
| 8,018,164 B2 | 9/2011 | Shannon et al. |
| 8,231,219 B2 | 7/2012 | Weeber |
| 8,241,354 B2 | 8/2012 | Hong et al. |
| 8,382,281 B2 | 2/2013 | Weeber |
| 8,430,508 B2 | 4/2013 | Weeber |
| 8,480,228 B2 | 7/2013 | Weeber |
| 8,573,775 B2 | 11/2013 | Weeber |
| 8,747,466 B2 | 6/2014 | Weeber et al. |
| 8,770,745 B2 | 7/2014 | Lindacher et al. |
| 8,862,447 B2 | 10/2014 | Weeber |
| 9,335,563 B2 | 5/2016 | Weeber |
| 2001/0035935 A1 | 11/2001 | Bhalakia et al. |
| 2001/0051825 A1 | 12/2001 | Peterson |
| 2002/0118337 A1 | 8/2002 | Perrott et al. |
| 2002/0173846 A1 | 11/2002 | Blake et al. |
| 2002/0196408 A1 | 12/2002 | Bhalakia et al. |
| 2002/0196412 A1 | 12/2002 | Abitbol |
| 2003/0076478 A1 | 4/2003 | Cox |
| 2003/0171808 A1 | 9/2003 | Phillips |
| 2004/0054358 A1 | 3/2004 | Cox |
| 2004/0068317 A1 | 4/2004 | Knight |
| 2004/0085515 A1 | 5/2004 | Roffman et al. |
| 2004/0106992 A1 | 6/2004 | Lang et al. |
| 2004/0111153 A1 | 6/2004 | Woods et al. |
| 2004/0150790 A1 | 8/2004 | Roffman et al. |
| 2004/0156014 A1 | 8/2004 | Piers et al. |
| 2004/0167622 A1 | 8/2004 | Sunalp et al. |
| 2005/0096226 A1 | 5/2005 | Stock et al. |
| 2005/0125056 A1 | 6/2005 | Deacon et al. |
| 2005/0128432 A1 | 6/2005 | Altmann |
| 2005/0203619 A1 | 9/2005 | Altmann |
| 2005/0251254 A1 | 11/2005 | Brady et al. |
| 2005/0267575 A1 | 12/2005 | Nguyen et al. |
| 2006/0009816 A1 | 1/2006 | Fang et al. |
| 2006/0030938 A1 | 2/2006 | Altmann |
| 2006/0066808 A1 | 3/2006 | Blum et al. |
| 2006/0068453 A1 | 3/2006 | Altieri |
| 2006/0109421 A1 | 5/2006 | Ye et al. |
| 2006/0116763 A1 | 6/2006 | Simpson |
| 2006/0116764 A1 | 6/2006 | Simpson |
| 2006/0116765 A1 | 6/2006 | Blake et al. |
| 2006/0238702 A1 | 10/2006 | Glick et al. |
| 2006/0244904 A1 | 11/2006 | Hong et al. |
| 2006/0244916 A1 | 11/2006 | Guillon |
| 2006/0279700 A1 | 12/2006 | Liang |
| 2007/0052920 A1 | 3/2007 | Stewart et al. |
| 2007/0129803 A1 | 6/2007 | Cumming et al. |
| 2007/0171362 A1 | 7/2007 | Simpson et al. |
| 2007/0182924 A1 | 8/2007 | Hong et al. |
| 2007/0268453 A1 | 11/2007 | Hong et al. |
| 2007/0279585 A1 | 12/2007 | Bartoli |
| 2008/0018910 A1 | 1/2008 | Neal et al. |
| 2008/0030677 A1 | 2/2008 | Simpson |
| 2008/0161914 A1 | 7/2008 | Brady et al. |
| 2008/0231809 A1 | 9/2008 | Haigis |
| 2008/0273169 A1 | 11/2008 | Blum et al. |
| 2008/0291393 A1 | 11/2008 | Menezes |
| 2009/0012609 A1 | 1/2009 | Geraghty et al. |
| 2009/0036980 A1 | 2/2009 | Norrby et al. |
| 2009/0051876 A1 | 2/2009 | Seiler et al. |
| 2009/0062911 A1 | 3/2009 | Bogaert |
| 2009/0088840 A1 | 4/2009 | Simpson et al. |
| 2009/0164008 A1 | 6/2009 | Hong et al. |
| 2009/0210054 A1* | 8/2009 | Weeber ............... A61F 2/1613 623/6.11 |
| 2009/0234448 A1 | 9/2009 | Weeber et al. |
| 2009/0279048 A1 | 11/2009 | Hong et al. |
| 2009/0323020 A1 | 12/2009 | Zhao et al. |
| 2010/0016965 A1 | 1/2010 | Hong et al. |
| 2010/0082017 A1 | 4/2010 | Zickler et al. |
| 2010/0100178 A1 | 4/2010 | Weeber et al. |
| 2010/0161048 A1 | 6/2010 | Schaper, Jr. |
| 2010/0274234 A1 | 10/2010 | Liang |
| 2012/0078239 A1 | 3/2012 | Reinstein et al. |
| 2012/0123534 A1 | 5/2012 | Yoon et al. |
| 2012/0140166 A1 | 6/2012 | Zhao |
| 2012/0143326 A1 | 6/2012 | Canovas Vidal et al. |
| 2012/0320334 A1 | 12/2012 | Ho et al. |
| 2013/0335701 A1 | 12/2013 | Canovas Vidal et al. |

FOREIGN PATENT DOCUMENTS

| | | |
|---|---|---|
| CN | 1039487 A | 2/1990 |
| CN | 1406120 A | 3/2003 |
| CN | 1833192 A | 9/2006 |
| DE | 8107675 U1 | 7/1981 |
| EP | 226400 A2 | 6/1987 |
| EP | 227357 A2 | 7/1987 |
| EP | 0343067 A1 | 11/1989 |
| EP | 0457553 A2 | 11/1991 |
| EP | 681198 A1 | 11/1995 |
| EP | 0926531 A1 | 6/1999 |
| EP | 949529 A2 | 10/1999 |
| EP | 957331 A2 | 11/1999 |
| EP | 1424049 A1 | 6/2004 |
| EP | 1310267 B1 | 1/2008 |
| EP | 1424049 B1 | 6/2009 |
| EP | 2182891 B1 | 4/2014 |
| FR | 2745711 A1 | 9/1997 |
| JP | H0255314 A | 2/1990 |
| WO | 8603961 A1 | 7/1986 |
| WO | 9222264 A1 | 12/1992 |
| WO | 9303409 A1 | 2/1993 |
| WO | 9507487 A1 | 3/1995 |
| WO | 9856315 A1 | 12/1998 |
| WO | 0019906 A1 | 4/2000 |
| WO | 0111418 A1 | 2/2001 |
| WO | 0135868 A1 | 5/2001 |
| WO | 0154569 A1 | 8/2001 |
| WO | 0163344 A1 | 8/2001 |
| WO | 0182839 A1 | 11/2001 |
| WO | 0189424 A1 | 11/2001 |
| WO | 0221194 A2 | 3/2002 |
| WO | 03009053 A1 | 1/2003 |
| WO | 2004034129 A1 | 4/2004 |
| WO | 2004090611 A2 | 10/2004 |
| WO | 2004096014 A2 | 11/2004 |
| WO | 05019906 A1 | 3/2005 |
| WO | 06025726 A1 | 3/2006 |
| WO | 2006032263 A2 | 3/2006 |
| WO | 2006047698 A1 | 5/2006 |
| WO | 06060477 A2 | 6/2006 |
| WO | 2006060480 A2 | 6/2006 |
| WO | 2007067872 A2 | 6/2007 |
| WO | 2007092948 A1 | 8/2007 |
| WO | 2007133384 A2 | 11/2007 |
| WO | 2008045847 A2 | 4/2008 |
| WO | 2008083283 A2 | 7/2008 |
| WO | 2009020963 A1 | 2/2009 |

(56) References Cited

FOREIGN PATENT DOCUMENTS

| WO | 2009029515 A1 | 3/2009 |
| --- | --- | --- |
| WO | 2009058755 A1 | 5/2009 |
| WO | 2009076670 A1 | 6/2009 |
| WO | 2009137491 A1 | 11/2009 |
| WO | 2010009254 A1 | 1/2010 |
| WO | 2010009257 A1 | 1/2010 |
| WO | 2011028659 A1 | 3/2011 |
| WO | 2013080053 A1 | 6/2013 |

OTHER PUBLICATIONS

Zheleznyak L., et al., "Modified Monovision to Improve Binocular Through-Focus Visual Performance," ARVO Meeting Abstracts Apr. 22, 2011, Apr. 4, 2011, [retrieved on May 8, 2013], Retrieved from the Internet.

Alfonso J.F., et al., "Prospective Study of the Acri.LISA Bifocal Intraocular Lens," Journal of Cataract Refractive Surgery, Nov. 2007, vol. 33 (11), pp. 1930-1935.

Alio J.L., et al., "Phakic Anterior Chamber Lenses for the Correction of Myopia: A 7-Year Cumulative Analysis of Complications in 263 Cases," Ophthalmology, Mar. 1999, vol. 106 (3), pp. 458-466.

Apple D.J., et al., "Anterior Chamber Lenses Part 1: Complications and Pathology and a Review of Designs," Journal of Cataract Refractive Surgery, Mar. 1987, vol. 13 (2), pp. 157-174.

Apple D.J., et al., Eds., "Intraocular Lenses: Evolution, Designs, Complications and Pathology," in: New Concepts in Intraocular Lens Implantation, Williams & Wilkins publisher, Jan. 1989, vol. 22 (36), pp. 205-221.

Apple D.J., et al., Eds., "Intraocular Lenses: Evolution, Designs, Complications and Pathology," in: New Concepts in Intraocular Lens Implantation, Williams & Wilkins publisher, Jan. 1989, vol. 36 (1), pp. 21-36.

Baikoff G., et al., "Angle-fixated Anterior Chamber Phakic Intraocular Lens for Myopia 7 to -19 Diopters," Journal of Refractive Surgery, May-Jun. 1998, vol. 14 (3), pp. 282-292.

Canovas C., et al., "Hybrid Adaptive-Optics Visual Simulator," Optical Letters, Jan. 15, 2010, vol. 35 (2), pp. 196-198.

Cheng X., et al., "Predicting Subjective Judgment of Best Focus with Objective Image Quality Metrics," Journal of Vision, Apr. 2004, vol. 4 (4), pp. 310-321.

Cilco Advertisement Brochure, Oct. 1982, 3 pages.

Cohen A.L., "Practical Design of a Bifocal Hologram Contact Lens or Intraocular Lens," Applied Optics, Jul. 1, 1992, vol. 31 (19), pp. 3750-3754.

De Almeida M.S., et al., "Different Schematic Eyes and their Accuracy to the in Vivo Eye: A Quantitative Comparison Study," Brazilian Journal of Physics, Jun. 2007, vol. 37 (2A), 10 pages.

Diffractive Lenses for Extended Depth of Focus and Presbyopic Correction, Presentation from Wavefront Congress held on Feb. 15, 2008, Rochester, New York.

Doskolovich L.L., et al., "Special Diffractive Lenses," Lens and Optical Systems Design, Apr. 1992, vol. 1780, pp. 393-402.

Kim J.H., et al., "The Analysis of Predicted Capsular Bag Diameter using Modified Model of Capsule Measuring Ring in Asians," Clinical and Experimental Ophthalmology, Apr. 2008, vol. 36 (3), pp. 238-244.

Liou H.L., et al., "Anatomically Accurate, Finite Model Eye for Optical Modeling," Journal of Optical Society of America, Aug. 1997, vol. 14 (8), pp. 1684-1695.

Liou H.L., et al., "The Prediction of Spherical Aberration with Schematic Eyes," Ophthalmic and Physiological Optics, Jan. 1996, vol. 16 (4), pp. 348-354.

Marinho A., "Results are Encouraging for Phakic IOLs, but More Work is needed," Refractive Surgery, Feb. 2000, p. 12, 15.

Marsack J.D., et al., "Metrics of Optical Quality Derived from Wave Aberrations Predict Visual Performance," Journal of Vision, Apr. 2004, vol. 4 (4), pp. 322-328.

Menapace R., "The Capsular Tension Rings," Journal of Cataract & Refractive Surgery, Dec. 10, 2008, Chap. 3, pp. 27-44.

Monsoriu J.A., et al., "Devil's Lenses," Optics Express, Oct. 17, 2007, vol. 15 (21), pp. 13858-13864.

Navarro R., et al., "Accommodation-Dependent Model of the Human Eye with Aspherics," Journal of the Optical Society of America, Aug. 1985, vol. 2 (8), pp. 1273-1281.

Nio Y.K., et al., "Effect of Intraocular Lens Implantation on Visual Acuity, Contrast Sensitivity, and Depth of Focus," Journal of Cataract and Refractive Surgery, Nov. 2003, vol. 29 (11), pp. 2073-2081.

Norrby S., et al., "Model Eyes for Evaluation of Intraocular Lenses," Applied Optics, Sep. 7, 2007, vol. 46 (26), pp. 6595-6605.

Olsen T., "Simple Method to Calculate the Surgically Induced Refractive Change," Journal of Cataract & Refractive Surgery, Mar. 1993, vol. 19 (2), pp. 319-320.

Piers P.A., et al., "Eye Models for the Prediction of Contrast Vision in Patients with New Intraocular Lens Designs," Optics Letters, Apr. 1, 2004, vol. 29 (7), pp. 733-735.

Piers P.A., et al., "Theoretical Comparison of Aberration-Correcting Customized and Aspheric Intraocular Lenses," Journal of Refractive Surgery, Apr. 2007, vol. 23 (4), pp. 374-384.

Praeger D.L., "Praeger Technique for the Insertion of the Copeland Radial IOL Posterior Chamber Placement," Copeland Lens, 1982, 7 pages.

Siedlecki D., et al., "Radial Gradient index Intraocular Lens: a Theoretical Model," Journal of Modern Optics, Feb. 20-Mar. 10, 2008, vol. 55 (4-5), pp. 639-647.

Strenn K., et al., "Capsular bag Shrinkage after Implantation of an Open-Loop Silicone Lens and a Poly(methyl methacrylate) Capsule Tension Ring," Journal of Cataract and Refractive Surgery, Dec. 1997, vol. 23 (10), pp. 1543-1547.

Tehrani M., et al., "Capsule Measuring Ring to Predict Capsular Bag Diameter and Follow its Course after Foldable Intraocular Lens Implantation," Journal of Cataract Refractive Surgery, Nov. 2003, vol. 29 (11), pp. 2127-2134.

Terwee T., et al., "Visualization of the Retinal Image in an Eye Model With Spherical and Aspheric, Diffractive, and Refractive Multifocal Intraocular Lenses," Journal of Refractive Surgery, Mar. 2008, vol. 24 (3), pp. 223-232.

Van Den Berg T.J., "Analysis of Intraocular Straylight, Especially in Relation to Age," Optometry and Vision Science, Feb. 1995, vol. 72 (2), pp. 52-59.

Van Meeteren A., "Calculations on the Optical Modulation Transfer Function of the Human Eye for White Light," Optica Acta, May 1974, vol. 21 (5), pp. 395-412.

Vass C., et al., "Prediction of Pseudophakic Capsular bag Diameter based on Biometric Variables," Journal of Cataract and Refractive Surgery, Oct. 1999, vol. 25 (10), pp. 1376-1381.

Venter, J.A., et al., "Visual Outcomes and Patient Satisfaction with a Rotational Asymmetric Refractive Intraocular Lens for Emmetropic Presbyopia," Cataract & Refractive Surgery, Mar. 2015, vol. 41 (3), pp. 585-593.

Villegas E.A., et al., "Correlation between Optical and Psychophy, Sical Parameters as a Function of Defocus," Optometry and Vision Science, Jan. 1, 2002, vol. 79 (1), pp. 60-67.

\* cited by examiner

LENSES, SYSTEMS AND METHODS FOR PROVIDING BINOCULAR CUSTOMIZED TREATMENTS TO CORRECT PRESBYOPIA

CROSS-REFERENCES TO RELATED APPLICATIONS

This application claims priority to and is a divisional of U.S. patent application Ser. No. 14/096,544, filed on Dec. 4, 2013, which claims priority to U.S. provisional application No. 61/733,292 filed on Dec. 4, 2012, the entire contents of which are incorporated herein by reference.

BACKGROUND OF THE INVENTION

Field of the Invention

This invention relates generally to correction of eye defects, and more specifically, to a system, method and apparatus for providing binocular customized treatments for remedying presbyopia.

Description of the Related Art

Surgery on the human eye has become commonplace in recent years. Many patients pursue eye surgery as an elective procedure to treat an adverse eye condition, such as to avoid the use of contact lenses or glasses. One eye condition that can be treated surgically is presbyopia. A patient suffering from presbyopia lacks the capability of the eye lens to accommodate or bend and thus to see at far distance and at near distance. Presbyopia can be induced by age and/or pseudophakia (a condition in which a natural lens has been replaced with an intraocular lens).

Several treatment options are available for presbyopia. For example, multifocal intraocular lenses, extended depth of focus lenses, corneal inlays or other accommodating intraocular lenses can be surgically implanted in the eye of a patient suffering from presbyopia to allow the patient to focus and refocus between near and far objects. Another treatment option available to patients suffering from presbyopia is based on monovision. In this option, generally the dominant eye is targeted for distant vision and the non-dominant eye is targeted for near vision. This can be achieved by implanting the dominant eye with an intraocular lens (IOL) having a power that achieves plano refraction such that the dominant eye has no refractive error and by implanting the non-dominant eye with an IOL that has an add power between 1.0-2.0 Diopter over the dominant eye.

However, such an approach can result in sub-optimal intermediate vision if the non-dominant eye is targeted for near vision or sub-optimal near vision if the non-dominant eye is targeted for intermediate vision. Additionally, some patients may not tolerate the refractive differences in the dominant and non-dominant eye.

SUMMARY OF THE INVENTION

Multifocal intraocular lenses (IOLs) providing two or more optical powers, for example, one for near vision and one for distant vision, can be implanted in the eye of a patient suffering from presbyopia to overcome some of the disadvantages of monovision. Although multifocal IOLs can lead to improved quality of vision for many patients, some patients can experience undesirable visual effects (dysphotopsia), e.g. glare or halos. For example, if light from a distant point source is imaged onto the retina by the distant focus of a multifocal IOL, the near focus of the multifocal IOL will simultaneously superimpose a defocused image on top of the image formed by the distant focus. This defocused image may manifest itself in the form of a ring of light surrounding the in-focus image, and is referred to as a halo. Rotationally symmetric multifocal designs present symmetric halo shapes, while non-rotationally symmetric multifocal lenses present asymmetric halos. Additionally, intermediate vision may be compromised in multifocal IOLs that are configured to provide near and distant vision.

Thus, there exists a need for an ophthalmic solution that provides improved vision at all of near, far and intermediate distances while reducing dysphotopsia. One approach to provide improved vision at all of near, far and intermediate distances while reducing dysphotopsia can be a lens with an extended depth of focus. Without subscribing to any particular, a lens with an extended depth of focus can image objects with a certain distance of its focal point with acceptable sharpness on the retina. Thus, an extended depth of focus lens can produce images with acceptable sharpness for objects located at intermediate to far distances or for objects located at near to intermediate distances. Various techniques for extending the depth of focus of a lens have been proposed. For example, some approaches are based on intraocular lenses with refractive or diffractive zones with different powers.

The embodiments disclosed herein include various ophthalmic lens solutions (such as, for example, contact lenses, IOLs, phakic IOLs, corneal inlays, as well as corneal reshaping procedures such as, laser treatments, or combinations of thereof etc.) for treating ophthalmic conditions in both eyes to enhance visual acuity at near, intermediate and far distances, and therefore provide a full range of vision. In various embodiments disclosed herein, binocular extension of depth of focus is achieved by inducing rotationally symmetric aberrations (e.g. fourth and/or higher order spherical aberrations) in one eye and by inducing non-rotationally symmetric aberrations (e.g. astigmatism, coma and/or trefoil) in the other eye to enhance visual acuity at an intermediate distance. In another aspect, binocular extension of depth of focus is achieved by a rotationally symmetric diffractive lens solution in one eye and a rotationally asymmetric diffractive lens solution in the other eye. In another aspect, binocular extension of depth of focus is achieved by a rotationally symmetric refractive lens solution in one eye and a rotationally asymmetric refractive lens solution in the other eye. In another aspect, visual acuity at an intermediate distance can be enhanced by applying scaled version of natural aberrations that are present in the patient's eye, as referred in U.S. patent application Ser. No. 13/690,505 filed on Nov. 30, 2012 and entitled Lenses, Systems and Methods For Providing Custom Aberration Treatments And Monovision To Correct Presbyopia which is incorporated herein by reference, in addition to inducing rotationally symmetric and asymmetric aberrations. In an alternative embodiment, the aberration patterns (e.g. fourth and/or higher order spherical aberrations and astigmatism, coma and/or trefoil) may also be imposed on the top of monovision, achieved with either refractive or diffractive techniques or on the top of a mix and match of multifocal or extended depth of focus lenses, which may also combine symmetric and asymmetric concepts binocularly.

In various embodiments, a binocular vision simulator can be used to determine the amount and type of aberrations to be induced in each eye. The combination that provides the best through focus performance as well as the patient's comfort is chosen. An example method of implementing the concepts discussed herein includes: (i) determining with a binocular vision simulator a first amount of rotationally symmetric or non-rotationally symmetric aberration which provides visual acuity for intermediate and distant vision in a first eye; (ii) determining with the binocular vision simulator a second amount of rotationally symmetric or non-rotationally symmetric aberration which provides visual acuity for intermediate and near vision in a second eye; (iii) applying the first amount of rotationally symmetric or non-rotationally symmetric aberration in the first eye; and (iv) applying the second amount of non-rotationally symmetric or rotationally symmetric aberration in the second eye, wherein a rotationally symmetric aberration pattern is applied to the second eye if a non-rotationally symmetric aberration pattern is applied to the first eye and vice-versa. Binocular visual acuity or just visual perception at different defocus position may be tested in those conditions. The test may also be performed in the presence of rotationally symmetric and asymmetric diffractive profiles once applied using the binocular visual simulator, with a goal of determining the combination of aberrations and diffractive ophthalmic solutions which provide a continuous range of vision.

Various embodiments disclosed herein include lenses, methods and systems that can correct presbyopia by extending the depth of focus for lenses that are configured to provide distant or near vision such that improved intermediate vision is provided by binocular summation.

BRIEF DESCRIPTION OF THE DRAWINGS

Understanding of the present invention will be facilitated by consideration of the following detailed description of the preferred embodiments of the present invention taken in conjunction with the accompanying drawings, in which like numerals refer to like parts, and in which:

FIG. 4A1-4A5 shows various embodiments of lenses having rotationally asymmetric diffractive features.

DETAILED DESCRIPTION OF THE PREFERRED EMBODIMENT

It is to be understood that the figures and descriptions of the present invention have been simplified to illustrate elements that are relevant for a clear understanding of the present invention, while eliminating, for the purpose of clarity, many other elements found in typical lenses, lens systems and lens design methods. Those of ordinary skill in the arts can recognize that other elements and/or steps are desirable and may be used in implementing the embodiments described herein.

The embodiments described herein are directed to an ophthalmic lens, such as an intraocular lens (IOL), or a corneal implant, and other vision correction methodologies, such as laser treatments, and a system and method relating to same, for providing rotationally symmetric aberration patterns in one eye and non-rotationally symmetric aberration patterns in the other eye in order to induce a binocular customized treatment that achieves visual acuity at a range of distances.

The terms "power" or "optical power" are used herein to indicate the ability of a lens, an optic, an optical surface, or at least a portion of an optical surface, to redirect incident light for the purpose of forming a real or virtual focal point. Optical power may result from reflection, refraction, diffraction, or some combination thereof and is generally expressed in units of Diopters. One of ordinary skill in the art will appreciate that the optical power of a surface, lens, or optic is generally equal to the reciprocal of the focal length of the surface, lens, or optic, when the focal length is expressed in units of meters.

Figure 1:
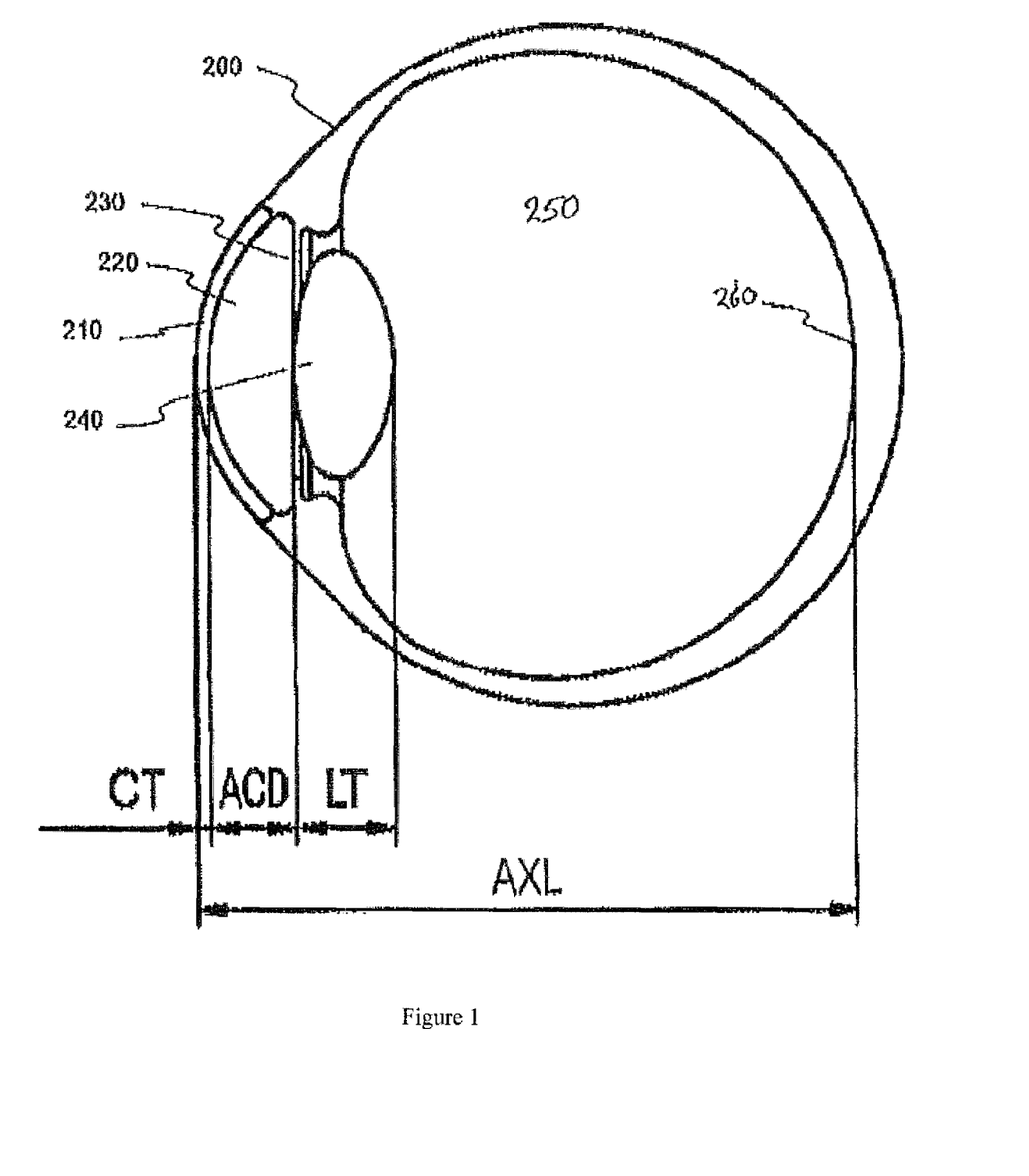
FIG. 1 is a diagram illustrating the relevant structures and distances of the human eye.

FIG. 1 is a schematic drawing of a human eye 200. Light enters the eye from the left of FIG. 1, and passes through the cornea 210, the anterior chamber 220, a pupil defined by the iris 230, and enters lens 240. After passing through the lens 240, light passes through the vitreous chamber 250, and strikes the retina 260, which detects the light and converts it to a signal transmitted through the optic nerve to the brain (not shown). Cornea 210 has corneal thickness (CT), which is the distance between the anterior and posterior surfaces of the center of the cornea 210. Anterior chamber 220 has an anterior chamber depth (ACD), which is the distance between the posterior surface of the cornea 210 and the anterior surface of the lens 240. Lens 240 has lens thickness (LT) which is the distance between the anterior and posterior surfaces of the lens 240. The eye has an axial length (AXL) which is the distance between the center of the anterior surface of the cornea 210 and the fovea of the retina 260, where the image is focused.

The anterior chamber 220 is filled with aqueous humor, and optically communicates through the lens 240 with the vitreous chamber 250. The vitreous chamber 250 is filled with vitreous humor and occupies the largest volume in the eye. The average adult eye has an ACD of about 3.15 mm, although the ACD typically shallows by about 0.01 mm per year. Further, the ACD is dependent on the accommodative state of the lens, i.e., whether the lens 240 is focusing on an object that is near or far.

The quality of the image that reaches the retina is related to the amount and type of optical aberrations that each patient's eye presents. The ocular surfaces that generally contribute to ocular aberrations are the anterior cornea and the lens. Although, all optical aberrations will affect the quality (e.g. blur) of the image produced on the eye, some aberrations do not necessarily affect the sharpness and the clarity of the object as seen by the patient due to neural compensation. Various embodiments described herein take into account the neural compensation that allows a patient to perceive objects sharply and clearly even in the presence of optical aberrations.

The term "near vision," as used herein, refers to vision provided by at least a portion of the natural lens in a phakic eye or an intraocular lens in a pseudophakic eye, wherein objects relatively close to a patient are substantially in focus on the retina of the patient's eye. The term "near vision" generally corresponds to the vision provided when objects are at a distance from the patient's eye of between about 25 cm to about 50 cm. The term "distant vision" or "far vision," as used herein, refers to vision provided by at least a portion of the natural lens in a phakic eye or an intraocular lens in a pseudophakic eye, wherein objects relatively far from the patient are substantially in focus on the retina of the patient's eye. The term "distant vision" generally corresponds to the vision provided when objects are at a distance of at least about 2 m or greater. As used herein, the "dominant eye" is defined as the eye of the patient that predominates for distant vision, as defined above. The term "intermediate vision," as used herein, refers to vision provided by at least a portion of the natural lens in a phakic eye or an intraocular lens in a pseudophakic eye, wherein objects at an intermediate distance from the patient are substantially in focus on the retina of the patient's eye. Intermediate vision generally corresponds to vision provided when objects are at a distance of about 2 m to about 50 cm from the patient's eye.

As used herein, an IOL refers to an optical component that is implanted into the eye of a patient. The IOL comprises an optic, or clear portion, for focusing light, and may also include one or more haptics that are attached to the optic and serve to center the optic in the eye between the pupil and the retina along an optical axis. In various implementations, the haptic can couple the optic to zonular fibers of the eye. The optic has an anterior surface and a posterior surface, each having a particular shape that contributes to the refractive properties of the lens.

In the embodiments disclosed herein aberrations and/or additional optical power are provided in a patient's dominant and non-dominant eye to increase depth of focus and to provide improved distant, near and intermediate vision. In some embodiments, rotationally and/or non-rotationally symmetric aberrations can be induced in the patient's dominant and/or non-dominant eye, such that the patient is able to have visual acuity for a wide range of distances. In some embodiments, an optical add power between about +0.5 Diopters and +2.0 Diopters can be provided in addition to inducing rotationally and/or non-rotationally symmetric aberrations. In various embodiments, the optical power and the aberration pattern provided in each eye is selected such that one eye (e.g. the dominant eye) has an extended depth of focus to provide visual acuity at far and intermediate distances and the other eye (e.g. the non-dominant eye) has an extended depth of focus to provide visual acuity at near and intermediate distances. Improved visual acuity at an intermediate distance is obtained due to binocular summation, which is a process by which the brain combines the information it receives from the dominant and the non-dominant eye.

In one aspect, extended depth of focus can be obtained by implanting a first IOL in the first eye and a second IOL in the second eye. The first IOL is selected to have a first optical power and a first optical aberration pattern (e.g. rotationally symmetric or non-rotationally symmetric) to provide visual acuity above a certain threshold for objects located at far to intermediate distances. The second IOL is selected to have a second optical power and a second optical aberration pattern (e.g. rotationally symmetric or non-rotationally symmetric) to provide visual acuity above a certain threshold for objects located at near to intermediate distances. The IOLs can be monofocal or multifocal. In various embodiments, the IOLs can include diffractive features, which may also be rotationally symmetric or asymmetric. The IOLs may also include refractive features, which may also be rotationally symmetric or asymmetric.

In another aspect, extended depth of focus can be obtained by shaping the cornea and/or the lens of the first eye to have a first optical power and a first optical aberration pattern (e.g. rotationally symmetric or non-rotationally symmetric) to provide visual acuity above a certain threshold for objects located at far to intermediate distances; and shaping the cornea and/or the lens of the second eye to have a second optical power and a second optical aberration pattern (e.g. rotationally symmetric or non-rotationally symmetric) to provide visual acuity above a certain threshold for objects located at near to intermediate distances. The shaping of the cornea or the natural lens can be performed by known methods, such as, for example using picosecond or femtosecond laser. Laser ablation procedures can remove a targeted amount stroma of a cornea to change a cornea's contour and adjust for aberrations. In known systems, a laser beam often comprises a series of discrete pulses of laser light energy, with a total shape and amount of tissue removed being determined by a shape, size, location, and/or number of laser energy pulses impinging on a cornea. In an alternative embodiment, the treatment may combine laser and cataract surgery. While during cataract surgery, IOLs implanted may be generating the desired configuration of added powers, with either refractive or diffractive concepts, the combination of rotationally symmetric and non-rotationally symmetric aberrations may be created in a posterior laser treatment that may be applied either in the corneal or in these implanted IOLs. In some embodiments, extended depth of focus can be provided by designing a first lens for use in a first eye, and a second lens for use in a second eye. The first and the second lens can be corneal implants, contact lenses or lenses for use in spectacles. The first and second lenses can be monofocal or multifocal. The first lens has an optical power and an optical aberration pattern that provides distant to intermediate vision. The second lens has an optical power and an optical aberration pattern that provides near to intermediate vision.

In various embodiments described herein rotationally symmetric aberrations (e.g. fourth and higher order spherical aberration terms) are induced in one eye while non-rotationally symmetric aberrations (e.g. astigmatism, coma and trefoil or combination thereof) are induced in the other eye to provide extended depth of focus. In various embodiments, the rotationally symmetric and non-rotationally symmetric aberrations can be superimposed over the naturally occurring aberrations in the eye. In some embodiments, the naturally occurring aberrations in the patient's eye may be corrected or scaled, as detailed in U.S. patent application Ser. No. 13/690,505 referenced above, in addition to inducing the rotationally symmetric or non-rotationally symmetric aberrations.

Rotationally symmetric aberrations, such as, for example including higher order spherical aberration terms can generate a uniform blur. In some instances, this uniform blur can translate into rotationally symmetric halos. On the other hand, non-rotationally symmetric aberrations can generate asymmetric halos which may be more tolerable as compared to rotationally symmetric halos. Providing rotationally symmetric aberrations in one eye and non-rotationally symmetric aberrations in the other eye can advantageously improve intermediate vision and extend depth of focus while reducing the impairments caused by rotationally symmetric halos. In some instances, combining spherical and/or non-rotationally symmetric with monovision can also improve stereopsis, which is related to depth perception.

The amount and type of rotationally symmetric and non-rotationally symmetric aberrations to be induced in each eye can be tested. A visual simulator was used to study whether the amount of aberrations that can be induced to produce a loss of one line in visual acuity is constant through the population. In order to do that, the monocular visual acuity of 5 subjects was measured under cyclopegic conditions when natural aberrations were corrected and those corresponding with an average pseudophakic eye were induced (0.15 μm RMS for a 5 mm pupil). Then, the amount of either spherical aberration or positive vertical coma that produced a loss of visual acuity of 0.1 Log MAR was determined when a physical pupil of 4 mm was imposed. The threshold value for negative SA was the smallest (−0.16±0.04 μm at 5 mm pupil induction), followed by positive SA (0.25±0.05 μm). The custom threshold for VC was consistently the highest (0.78±0.12 μm), ranging from 0.70 to 0.98 μms. Therefore, it is safe to consider a threshold of vertical coma and spherical aberration of about 0.8 μm and 0.2 μm, respectively. Those are the values that may be imposed as rotationally symmetric (spherical aberration) and asymmetric (vertical coma), while possibly correcting natural aberrations and inducing those corresponding to the average pseudophakic eye. This application is particularly advantageous for these eyes with a dense cataract which may increase the difficulty of determining potential customized thresholds.

In another embodiment, the vision simulator can be used to individually determine these monocular thresholds to both rotationally and non rotationally symmetric aberrations. As described previously, the visual acuity can be measured at best focus for a certain pupil size (e.g. 3 mm pupil size, 4 mm pupil size, or 5 mm pupil size). Then, the letter size may be increased until the target visual acuity is reached (ie. that corresponding to the measured VA plus n*0.1 log MAR, being n is a number between 0 and 3). Different values of rotationally symmetric aberrations (e.g. higher order spherical aberrations) or non-rotationally symmetric aberrations (e.g. astigmatism, coma or trefoil) are applied to the eye and the threshold value of rotationally symmetric aberrations and non-rotationally symmetric aberrations is determined as the maximum amount of aberration that allows for resolving that letter size, and therefore, provides with measured VA plus n*0.1 log MAR. Once the monocular thresholds are determined for each eye, the corresponding values are presented binocularly to the subject. In one implementation, the binocular threshold values are the value of the rotationally/non-rotationally symmetric aberration that provides the best through focus as well as comfort for the patient. In some instances, an optical add power (e.g. between about +0.5 Diopters and +3.0 Diopters) can be provided to the non-domination and/or the dominant eye. In an alternative embodiment, rotationally symmetric and asymmetric diffractive designs can also be induced, for the patient to compare between different options.

Figure 2:
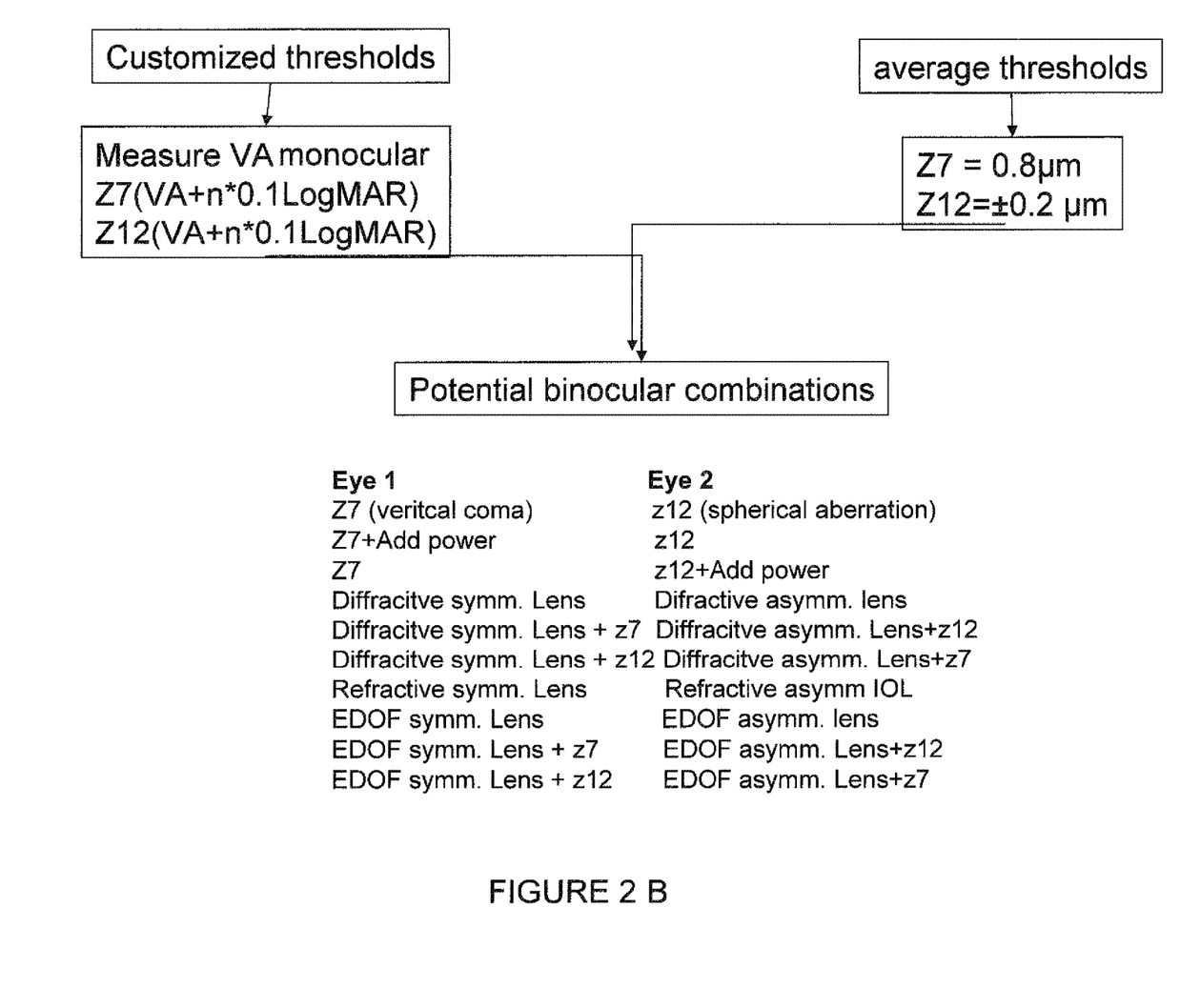
FIGS. 2A and 2B are flowcharts of an implementation of a method used to determine the combination of aberrations that can be induced to provide vision acuity at near, far and intermediate distances.
Figure 2A:
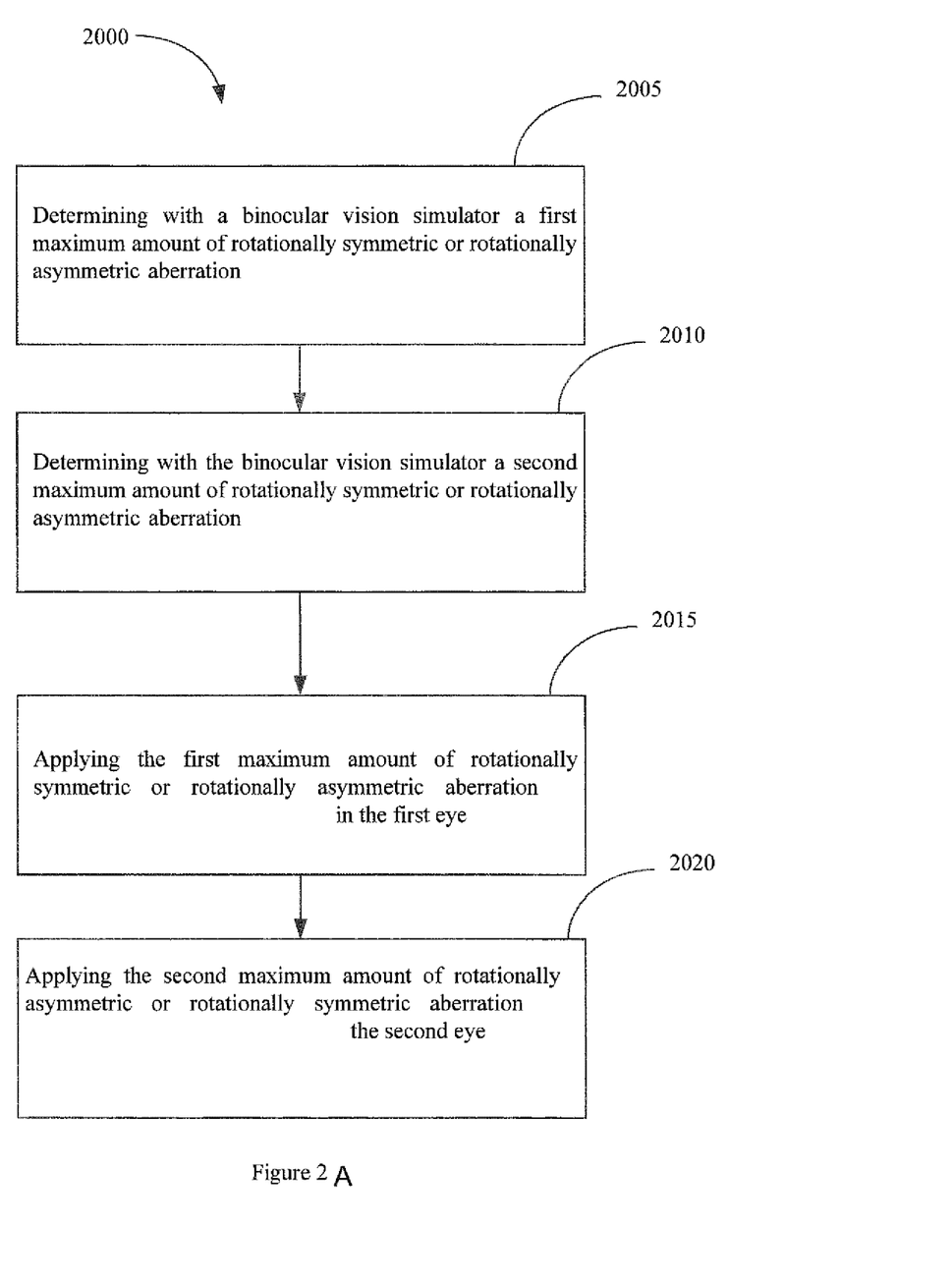

Another example method 2000 for determining the amount and type of rotationally symmetric and non-rotationally symmetric aberrations to be induced in each eye is illustrated in FIG. 2A. The method includes: (i) determining with a binocular vision simulator a first maximum amount of rotationally symmetric or non-rotationally symmetric aberration which provides distant vision in a first eye, as shown in block 2005; (ii) determining with the binocular vision simulator a second maximum amount of rotationally symmetric or non-rotationally symmetric aberration which provides near vision in a second eye, as shown in block 2010; (iii) applying the first maximum amount of rotationally symmetric or non-rotationally symmetric aberration in the first eye, as shown in block 2015; and (iv) applying the second maximum amount of non-rotationally symmetric or rotationally symmetric aberration in the second eye, as shown in block 2020. In various embodiments, a rotationally symmetric aberration pattern is applied to the second eye if a non-rotationally symmetric aberration pattern is applied in the first eye and vice-versa.

In one implementation of the method 2000 described above, the maximum amount of rotationally symmetric or non-rotationally symmetric aberration is that value selected from all possible values of rotationally symmetric or non-rotationally symmetric aberration which provides the highest extended depth of focus monocularly and the highest visual acuity at an intermediate distance binocularly. As previously discussed, the method 2000 can be implemented with IOLs, corneal implants, contact lenses, lenses for use in spectacles, etc. Alternately, the cornea or the lens of the patient can be shaped in accordance with the method 2000 such that rotationally/non-rotationally symmetric aberrations and an add power are induced in one eye to achieve distant vision with an extended depth of focus; and rotationally/non-rotationally symmetric aberrations and an add power are induced in the other eye to achieve near vision with an extended depth of focus.

An example of the procedure is shown at FIG. 2B, in which spherical aberration represents rotationally symmetric aberration term and vertical coma the non-rotationally symmetric aberration term. In order to select the treatment, the thresholds may be customized, while using a visual simulator as previously described or can be taken from those measured in the average population. Once the thresholds have been determined monocularly, the binocular test starts. Different options are shown in FIG. 2B. For a determined letter size, corresponding to a VA between 0 and 0.1 Log MAR, different viewing distances (0D of defocus, corresponding to far, −1.5 D of defocus corresponding to intermediate and −2.5 D of defocus corresponding to far) may be shown to a subject for him/her to subjectively judge the option that is more suitable or comfortable. This test can be performed before cataract surgery, in order to make a customized selection of the lens to implant for the patient and only if the degree of cataract allows for visual simulation. The test can be also performed after the surgery, when the resulting aberration patterns or added powers may be induced as a laser treatment either in the cornea or the IOL itself. FIG. 2B lists potential binocular combinations with the first combinations utilizing a purely refractive (mixed monovision) platform. Symmetric diffractive platforms in combination with asymmetric diffractive platforms as seen, for example, in FIGS. 4A1-4A5 may also be used. Symmetric refractive platforms along with asymmetric refractive platforms, such as seen in U.S. patent application Ser. No. 13/309,314, entitled filed on Dec. 1, 2011, and incorporated herein by reference in its entirety, may also be used.

The IOLs or other ophthalmic devices discussed for use herein may be constructed of any commonly employed material or materials used for rigid optics, such as polymethylmethacrylate (PMMA), or of any commonly used materials for resiliently deformable or foldable optics, such as silicone polymeric materials, acrylic polymeric materials, hydrogel-forming polymeric materials, such as polyhydroxyethylmethacrylate, polyphosphazenes, polyurethanes, and mixtures thereof and the like. The material used preferably forms an optically clear optic and exhibits biocompatibility in the environment of the eye. Additionally, foldable/deformable materials are particularly advantageous for formation of implantable ones of ophthalmic lenses for use in the present invention, in part because lenses made from such deformable materials may be rolled, folded or otherwise deformed and inserted into the eye through a small incision.

In addition to providing visual acuity at near, intermediate and far distances, the ophthalmic solutions (e.g. IOLs, contact lenses, corneal implants, etc.) used herein can correct for other conditions of the eye. For example, the ophthalmic solution can be a toric lens for correcting astigmatism and include rotationally/non-rotationally symmetric aberrations to provide enhanced visual acuity. As another example, the ophthalmic solution can be an aspheric lens including rotationally/non-rotationally symmetric aberrations to provide enhanced visual acuity. As yet another example, the ophthalmic solution can be a combination of refractive and diffractive features that are rotationally/non-rotationally symmetric to provide enhanced visual acuity.

Figure 3:
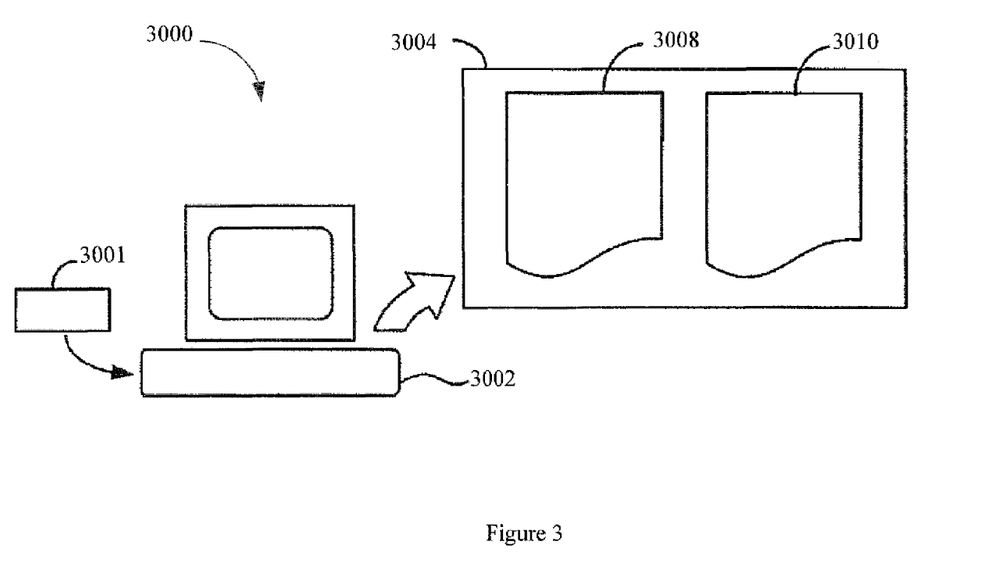
FIG. 3 is a diagram illustrating aspects of a system that can be used to implement the method described in FIG. 2.

The methods described herein can be performed by using instruments that are known to a person having ordinary skill in the art. An instrument to implement the methods described herein can comprise a set of apparatuses, including a set of apparatuses from different manufacturers that are configured to perform the necessary measurements and calculations. Any instrument comprising all needed measurements (ocular and corneal wavefront aberration measurements) as well as the needed calculations to implement the methods described herein, including but not limited to the method 2000 can be considered as an inventive embodiment. FIG. 3 is a block diagram illustrating an embodiment of a clinical system 3000 that can be used to implement the methods described herein, including but not limited to the method 2000. The system 3000 includes one or more apparatuses capable of performing the calculations, assessments and comparisons set forth in determining the rotationally/non-rotationally symmetric aberration patterns and the add power that provide enhanced visual acuity at near, intermediate and far distances. The system 3000 may include a biometric reader 3001 (e.g. a binocular vision simulator), a processor 3002, and a computer readable memory or medium 3004 coupled to the processor 3002. The computer readable memory 3004 includes therein an array of ordered values 3008 and sequences of instructions 3010 which, when executed by the processor 3002, cause the processor 3002 to select the rotationally/non-rotationally symmetric aberration pattern that provides distant vision with an extended depth of focus in one eye and near vision with an extended depth of focus in the other eye such that an enhanced visual acuity at an intermediate distance is obtained by binocular summation.

The array of ordered values 3008 can include one or more desired refractive outcomes, data obtained from measurements of the patient's eye, data related to one or more types of available ophthalmic solutions, a set of all possible rotationally/non-rotationally symmetric aberration patterns, parameters of refractive and diffractive features, etc. In some embodiments, the sequence of instructions 3010 can include algorithms to perform calculations, customization, simulation, comparison, etc.

The processor 3002 may be embodied in a general purpose desktop, laptop, tablet or mobile computer, and/or may comprise hardware and/or software associated with inputs 3001. In certain embodiments, the system 3000 may be configured to be electronically coupled to another device, such as one or more instruments for obtaining measurements of an eye or a plurality of eyes. Alternatively, the system 3000 may be adapted to be electronically and/or wirelessly coupled to one or more other devices.

The system illustrated in FIG. 3 can be used for selecting the rotationally/non-rotationally symmetric optical aberration patterns in blocks 2005 and 2010 of the method 2000. For example, the clinical measurements provided by the reader 3001, can be used to determine which rotationally/non-rotationally symmetric optical treatments stored in the processor 3002 provides distant vision with an extended depth of focus in one eye and near vision with an extended depth of focus in the other eye such that an enhanced visual acuity at an intermediate distance is obtained by binocular summation.

As discussed above, the methods described herein can be implemented in lenses (e.g. IOLs, contact lenses, lenses for use with spectacles, etc.). For example, in some embodiments, the lenses can be monofocal lenses that provide distant or near vision that include rotationally/non-rotationally symmetric aberration pattern for providing visual acuity for object located at intermediate distance. As another example, in some embodiments, the lenses can be multifocal lenses providing distant and near vision and further including rotationally/non-rotationally symmetric aberration pattern for providing visual acuity for object located at intermediate distance. As yet another example, in some embodiments, the lenses can have refractive or diffractive features that are symmetric or asymmetric such that improved visual acuity at near, intermediate and far distances is obtained. Some examples of lenses including rotationally asymmetric features that provide improved visual acuity at near, intermediate and far distances are discussed below with reference to FIGS. 4A1-4A5. As discussed above, rotationally symmetric aberrations can include higher order (e.g. $4^{th}$ and $6^{th}$ order) spherical aberrations. As discussed above, non-rotationally symmetric aberrations can include astigmatism, coma or trefoil.

Figure 4A:
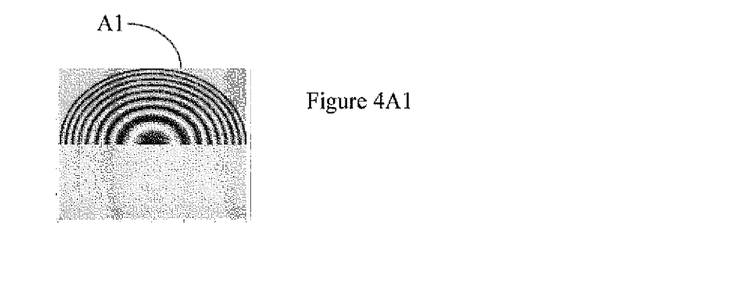

By way of example, FIGS. 4A1-4A5 shows various embodiments of lenses including rotationally asymmetric diffractive features. The lenses illustrated in FIGS. 4A1-4A5 include a plurality of partially annular structures. The partially annular structures can be distributed around a central optical zone disposed about an optical axis. In some embodiments, the optical zone between two consecutive partially annular structures can have an optical power that is equal to the optical power of the central zone. In some other embodiments, the optical zone between two consecutive partially annular structures can have an optical power that is different from the optical power of the central zone. Each of the partially annular structure can include microstructures that are diffractive or refractive. Each of the partially annular structure can have a vertical and horizontal profile that determines the overall optical power of the lens and the distribution of light between the various optical zones.

In FIG. 4A1, region A1 includes a plurality of semi-annular structures that cover about 50% of the surface area of the ophthalmic lens. The upper part of the lens has 50% light distribution between 1 D and 2 D add power, while the rest has an asymmetric light distribution between the same add powers. In various embodiments, the portion of the ophthalmic lens below the region A1 can be devoid of microstructures or include microstructures similar to the microstructures in the region A1, such that the ophthalmic lens illustrated in FIG. 4A1 is rotationally symmetric. In an alternative embodiment, the lower part may be composed by a different diffractive designs which provides different add powers and light distributions.

Figure 4A:
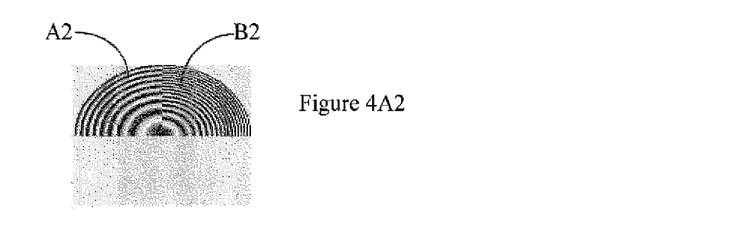

FIG. 4A2 illustrates an ophthalmic lens including a first region A2 having partially annular structures with an add power of 1 D, being essentially monofocal, and a second region B2 having partially annular structures with an add power of 2 D, also monofocal. The regions A2 and B2 can each occupy about 25% of the surface area of the ophthalmic lens, while the remaining approximately 50% of the lens has a 0D add power and its basically refractive monofocal.

Figure 4A:
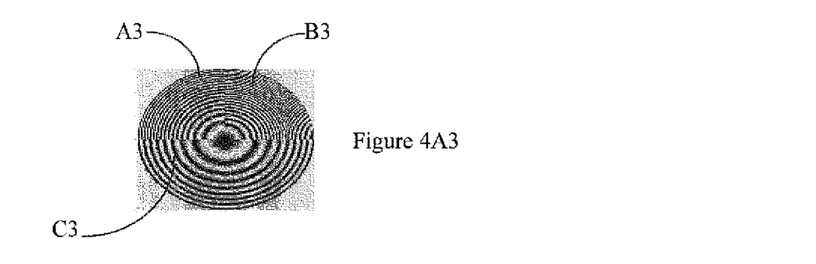
Figure 4A:
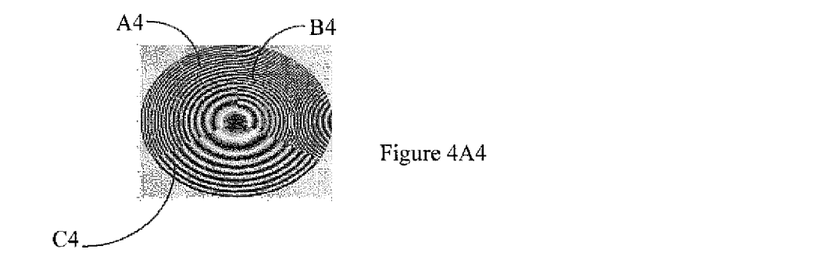
Figure 4A:
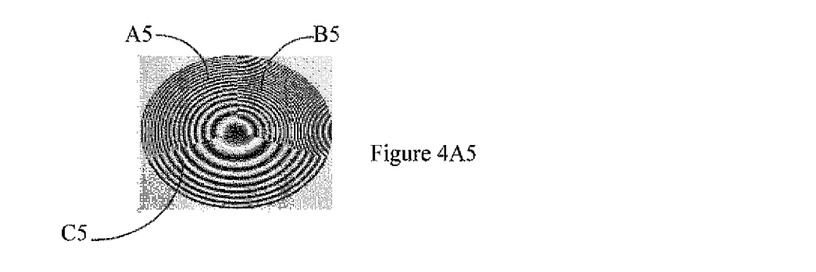

FIG. 4A3 illustrates an ophthalmic lens including a first region A3 having partially annular structures with an add power of 2 D, being essentially monofocal, a second region B3 having partially annular structures with an add power of 3 D, being essentially monofocal, and a third region C3 having partially annular structures with an add power of 1 D, being essentially monofocal. The regions A3 and B3 can each occupy about 25% of the surface area of the ophthalmic lens and the region C3 can occupy about 50% of the surface area of the ophthalmic lens. The area occupied by every different sector can be modified as shown in FIG. 4A4, where each region subtends the same area. In an alternative embodiment, at FIG. 4A5, the area occupied by the region with an add power of 1D is greater than for the rest.

Although the invention has been described and pictured in an exemplary form with a certain degree of particularity, it should be understood that the present disclosure of the exemplary form has been made by way of example, and that numerous changes in the details of construction and combination and arrangement of parts and steps may be made without departing from the spirit and scope of the invention as set forth in the claims hereinafter.

What is claimed is:

1. A pair of intraocular lenses comprising:
 a first intraocular lens sized and configured for implantation in a first eye of a patient, the first intraocular lens including rotationally symmetric aberrations configured to induce a predetermined amount of one or more fourth or higher order spherical aberrations in said first eye of the patient; and
 a second intraocular lens sized and configured for implantation in a second eye of a patient, the second intraocular lens including non-rotationally symmetric aberrations configured to induce a predetermined amount of one or more second or higher order asymmetrical aberrations in said second eye of the patient;
 wherein the predetermined amount of one or more fourth or higher order spherical aberrations is induced only in the first eye, and the predetermined amount of one or more second or higher order asymmetrical aberrations is induced only in the second eye; and
 wherein the predetermined amount of one or more fourth or higher order spherical aberrations and the predetermined amount of one or more second or higher order asymmetrical aberrations collectively achieve binocular depth of focus.

2. The pair of lenses of claim 1, wherein the first lens includes a symmetrical multifocal intraocular lens and the second lens includes an asymmetrical multifocal lens.

3. The pair of lenses of claim 1, wherein the first intraocular lens is configured to provide visual acuity above a predetermined threshold for objects located at far and intermediate distances or far and near distances and the second intraocular lens is configured to provide visual acuity above a predetermined threshold for objects located at far distances.

4. The pair of lenses of claim 3, wherein the non-rotationally symmetric aberrations are selected from the group consisting of: astigmatism, coma and trefoil.

5. The pair of lenses of claim 4, wherein the first intraocular lens is configured to provide visual acuity above a predetermined threshold for objects located at far and intermediate distances or far and near distances and the second intraocular lens is configured to provide visual acuity above a predetermined threshold for objects located at far distances.

6. The pair of lenses of claim 1, wherein the first lens includes an asymmetrical multifocal intraocular lens and the second lens includes a symmetrical monofocal lens.

* * * * *